United States Patent
Wakamatsu

(10) Patent No.: US 10,456,569 B2
(45) Date of Patent: Oct. 29, 2019

(54) METHOD OF PRODUCING TRANSDERMAL ABSORPTION SHEET FOR MEDICAL USE

(71) Applicant: FUJIFILM Corporation, Tokyo (JP)

(72) Inventor: Satoshi Wakamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 87 days.

(21) Appl. No.: 15/825,111

(22) Filed: Nov. 29, 2017

(65) Prior Publication Data
US 2018/0147399 A1    May 31, 2018

(30) Foreign Application Priority Data

Nov. 30, 2016 (JP) ................................. 2016-233153

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 9/703* (2013.01);
(Continued)

(58) Field of Classification Search
CPC ........ A61M 37/015; A61M 2037/0023; A61M 2037/0046; A61M 2037/0053;
(Continued)

(56) References Cited

U.S. PATENT DOCUMENTS

| 2008/0269685 | A1* | 10/2008 | Singh ................ A61K 9/0021 604/173 |
| 2011/0006458 | A1* | 1/2011 | Sagi ................ A61M 37/0015 264/319 |
| 2015/0238413 | A1 | 8/2015 | Mochizuki et al. |

FOREIGN PATENT DOCUMENTS

| EP | 2283809 | 2/2011 |
| JP | 2009241357 | 10/2009 |

(Continued)

OTHER PUBLICATIONS

Wang et al., "Investigation on fabrication process of dissolving microneedle arrays to improve effective needle drug distribution", Eur J Pharm Sci., 66, pp. 148-156. (Jan. 23, 2015). (Year: 2015).*

(Continued)

*Primary Examiner* — Michael N Orlando
*Assistant Examiner* — Christopher W Raimund
(74) *Attorney, Agent, or Firm* — JCIPRNET

(57) ABSTRACT

The method of producing a transdermal absorption sheet includes, in this order, a filtration step of carrying out sterile filtration on a base liquid, a base liquid feeding step of feeding the base liquid to a surface of a mold having needle-like recessed portions, tip ends of which are filled with a drug solution, while leaving a space between the drug solution and the base liquid, a drying step of drying the drug solution and the base liquid, and a peeling-off step of peeling off a formed transdermal absorption sheet in which an average concentration of solid contents of the base liquid in the drying step is increased by 5% by weight or more from (Continued)

an average concentration in the base liquid feeding step, and then in a state in which the average concentration is 75% by weight or less, the base liquid is moved into the needle-like recessed portions.

3 Claims, 14 Drawing Sheets

(51) Int. Cl.
*A61K 9/70* (2006.01)
*A61K 8/02* (2006.01)
*A61K 38/38* (2006.01)
*B29L 31/00* (2006.01)
*A61K 47/36* (2006.01)

(52) U.S. Cl.
CPC .......... *A61K 8/0204* (2013.01); *A61K 38/385* (2013.01); *A61K 47/36* (2013.01); *A61M 2037/0046* (2013.01); *A61M 2037/0053* (2013.01); *B29L 2031/7544* (2013.01)

(58) Field of Classification Search
CPC . A61M 37/0015; A61K 9/0021; A61K 9/703; A61K 47/36; A61K 8/0204; A61K 38/385; B29L 2031/7544
See application file for complete search history.

(56) References Cited

FOREIGN PATENT DOCUMENTS

| | | |
|---|---|---|
| JP | 2013162982 | 8/2013 |
| WO | 2014077242 | 5/2014 |

OTHER PUBLICATIONS

Chu et al., "Fabrication of dissolving polymer microneedles for controlled drug encapsulation and delivery: Bubble and pedestal microneedle designs", J. Pharmaceutical Sciences, vol. 99, No. 10, pp. 4228-4238 (Apr. 5, 2010). (Year: 2010).*
"Search Report of Europe Counterpart Application", dated Apr. 6, 2018, p. 1-p. 8.

* cited by examiner

METHOD OF PRODUCING TRANSDERMAL ABSORPTION SHEET FOR MEDICAL USE

CROSS-REFERENCE TO RELATED APPLICATIONS

The present application claims priority under 35 U.S.C. § 119 to Japanese Patent Application No. 2016-233153, filed on Nov. 30, 2016. The above application is hereby expressly incorporated by reference, in its entirety, into the present application.

BACKGROUND OF THE INVENTION

1. Field of the Invention

The present invention relates to a method of producing a transdermal absorption sheet for medical use and particularly to a method of producing a transdermal absorption sheet for medical use by shape transfer using a mold having needle-like recessed portions formed thereon.

2. Description of the Related Art

As a method for administering a chemical or the like through a living body surface, that is, a skin, a mucous membrane, or the like, a chemical injection method of using a transdermal absorption sheet for medical use on which needle-like protruding portions having a high aspect ratio and containing a drug (hereinafter, also referred to as "microneedles") are formed and inserting the needle-like protruding portions into a skin is used.

As a method of producing a transdermal absorption sheet for medical use, for example, JP2013-162982A discloses a method of producing a microneedle sheet including feeding a non-drug-containing polymer solution on a mold in which a drug-containing polymer solution is solidified or semi-solidified, injecting the polymer solution into needle-like recessed portions by sucking the polymer solution using a pump, and then carrying out a drying treatment. WO2014/077242A discloses a method of producing a transdermal absorption sheet for medical use including forming a drug-containing layer which is dried and solidified in needle-like recessed portions of a mold, then applying a non-drug-containing solution to the drug-containing layer, and drying and solidifying the solution.

SUMMARY OF THE INVENTION

In production of a transdermal absorption sheet for medical use, since a non-drug-containing base liquid which fills the inside of needle-like recessed portions is surrounded by a mold and the upper side thereof is covered by another base liquid, there is a problem of taking a long time for drying. Since it takes a long time for drying, it is considered that the average concentration of the solid contents of the base liquid to be fed to the mold is increased to reduce the drying time. However, since a transdermal absorption sheet for medical use is for medical purpose, a step of carrying out sterile filtration on a liquid containing a material for the transdermal absorption sheet for medical use is required. In the sterile filtration, the viscosity of the base liquid has to be lowered to a certain degree to cause the base liquid to pass through a filtration membrane mesh having very fine pores. Therefore, the concentration of the solid contents of the base liquid cannot be increased.

The present invention is made in consideration of such circumstances and an object thereof is to provide a method of producing a transdermal absorption sheet for medical use capable of reducing the drying time for a base liquid at production while carrying out sterile filtration on the base liquid.

In order to achieve the above object, according to an aspect of the present invention, there is provided a method of producing a transdermal absorption sheet for medical use comprising, in this order: a filtration step of carrying out sterile filtration on a base liquid; a base liquid feeding step of feeding the base liquid to a surface of a mold having needle-like recessed portions, tip ends of which are filled with a drug solution, the needle-like recessed portions being formed on the surface, while leaving a space between the drug solution and the base liquid; a drying step of drying the drug solution and the base liquid; and a peeling-off step of peeling off a transdermal absorption sheet for medical use formed by drying the drug solution and the base liquid, in which an average concentration of solid contents of the base liquid in the drying step is increased by 5% by weight or more from an average concentration of solid contents of the base liquid in the base liquid feeding step, and then in a state in which the average concentration of the solid contents is 75% by weight or less, the base liquid is moved into each of the needle-like recessed portions of the mold.

According to the method of producing a transdermal absorption sheet for medical use according to the aspect of the present invention, after the base liquid is fed to the mold, drying is carried out until the average concentration of the solid contents of the base liquid is increased by 5% by weight or more. Then, the base liquid is moved into the needle-like recessed portions. Although the base liquid moved into the needle-like recessed portions is in a sealed state in which the vicinity thereof is surrounded by the mold, it is possible to reduce the drying time of the base liquid by drying the base liquid before moving the base liquid into the needle-like recessed portions.

In addition, in a case in which the base liquid is moved into the needle-like recessed portion, the average concentration of the solid contents of the base liquid is 75% by weight or less. Setting the average concentration of solid contents to 75% by weight or less allows the base liquid to have fluidity and thus the base liquid can be moved into the needle-like recessed portion.

Regarding the concentration of the solid contents of the base liquid fed to the mold, the concentrations of the solid contents and the concentration distributions are different in a thickness direction and in an in-plane direction by drying, and thus the "average concentration of the solid contents" is used as the concentration of the solid contents of the entire base liquid.

In the method of producing a transdermal absorption sheet for medical use according to the aspect of the present invention, it is preferable that the base liquid is moved into the needle-like recessed portions by carrying out suction from a side of the mold opposite to the surface on which the needle-like recessed portions are formed or by carrying out pressurization from the surface side of the mold on which the needle-like recessed portions are formed.

In the aspect of the present invention, a specific aspect of moving the base liquid into the needle-like recessed portions is shown and the base liquid can be moved into the needle-like recessed portions by the above method.

In the method of producing a transdermal absorption sheet for medical use according to the aspect, it is preferable that the base liquid feeding step is carried out in a state in which a moisture content of the drug solution is 20% by weight or more.

According to the aspect of the present invention, in a state in which the moisture content of the drug solution is 20% by weight or more, the base liquid feeding step is carried out and the drug solution and the base liquid are simultaneously dried in the following drying step so that the total drying time can be reduced. In addition, since the drug solution is dried in a high humidity environment in a state in which the solution is covered by the base liquid fed to the mold, the drug solution can be dried along the shape of the tip end of the needle-like protruding portion. Thus, it is possible to effectively fill the tip end with the drug solution.

According to the method of producing a transdermal absorption sheet for medical use of the present invention, it is possible to reduce the amount of drying in a sealed state after moving and to reduce the drying time by drying the base liquid before moving the base liquid into the needle-like recessed portions, moving the base liquid into the needle-like recessed portions in a state in which the base liquid is dried at a certain degree, and drying the base liquid.

DESCRIPTION OF THE PREFERRED EMBODIMENTS

Hereinafter, a method of producing a transdermal absorption sheet for medical use according to the present invention will be described with reference to the attached drawings. Incidentally, in the specification, numerical values indicated using the expression "to" mean a range including the numerical values indicated before and after the expression "to" as the lower limit and the upper limit.

Transdermal Absorption Sheet for Medical Use

Figure 1:
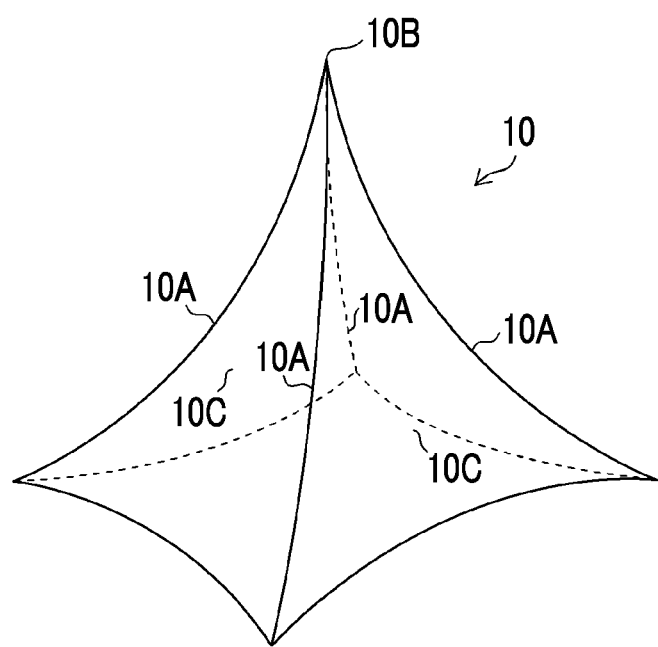
FIG. 1 is a perspective view showing a pyramidal microneedle (needle-like protruding portion) of a transdermal absorption sheet for medical use.
Figure 2:
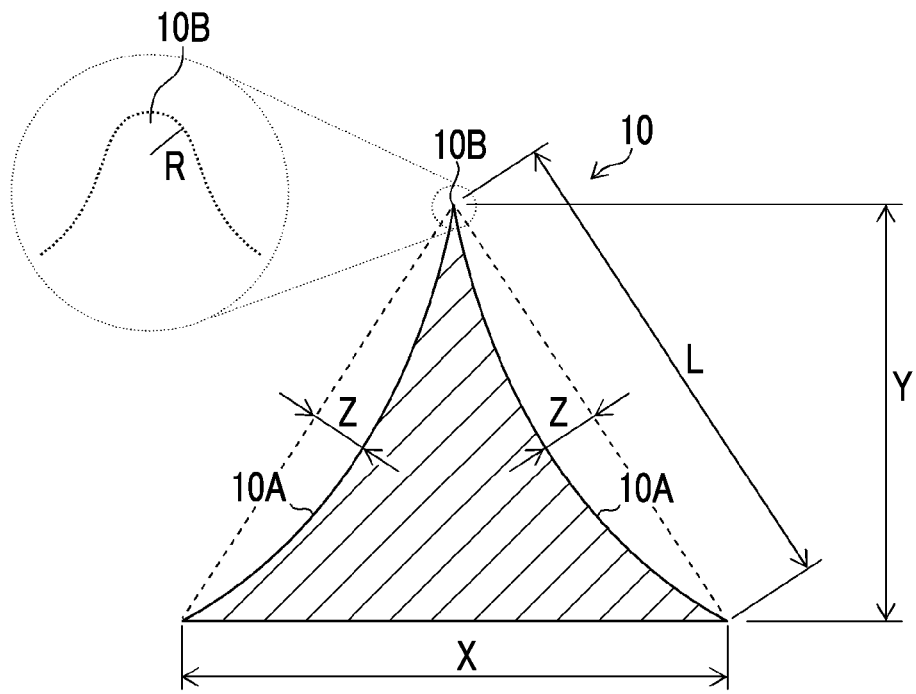
FIG. 2 is a cross-sectional view showing the pyramidal microneedle (needle-like protruding portion) of the transdermal absorption sheet for medical use.

Needle-like protruding portions (also referred to as microneedles) on a transdermal absorption sheet for medical use produced in an embodiment will be described. FIG. 1 is a perspective view showing a pyramidal microneedle (needle-like protruding portion) of a transdermal absorption sheet for medical use, and FIG. 2 is a cross-sectional view. In the embodiment, an example of a quadrangular pyramidal needle-like protruding portion is described, but the present invention is not limited to this shape.

As shown in FIGS. 1 and 2, it is preferable that a microneedle (needle-like protruding portion) 10 formed on the transdermal absorption sheet for medical use is shaped as follows so that the microneedle 10 can be stuck several hundred μm deep into the surface of the skin: (1) the tip end is sufficiently pointed, and the diameter of the needle penetrating the skin is sufficiently small (the aspect ratio of length/diameter is high), and (2) the microneedle has a sufficient strength (the needle does not bend).

Thus, to meet the requirement in (1), a thin and pointed shape is needed. However, this is opposed to (2), and an excessively thin needle is bent at the tip end or root thereof, whereas an excessively thick needle fails to be stuck into the skin. Thus, as shown in FIG. 1, a ridge line 10A of the microneedle 10 is preferably shaped to be curved toward the inside of the microneedle. The microneedle having such a shape can be made difficult to bend by widening the root while sufficiently sharpening the tip end. Further, the ridge lines 10A and 10A of a quadrangular pyramidal microneedle preferably extend from a quadrangular pyramidal surface 10C between the ridge lines.

The shape of the microneedle 10 is preferably formed such that one side X is in a range of 0.1 μm or more and 1,000 μm or less, and the height Y is 0.3 μm or more and 3,000 μm or less. More preferably, the one side X of the bottom surface is in a range of 10 μm or more and 400 μm or less and the height Y is 30 μm or more and 1,200 μm or less.

In a case in which the length of a segment connecting a start point and an end point of the ridge line is represented as L, the maximum depth Z of the curve of the ridge line 10A is preferably 0.04×L or more and 0.2×L or less. In addition, the radius of the curvature R of a microneedle tip end 10B, which indicates sharpness of the microneedle 10, is preferably 20 μm or less, and more preferably 15 μm or less.

Figure 3:
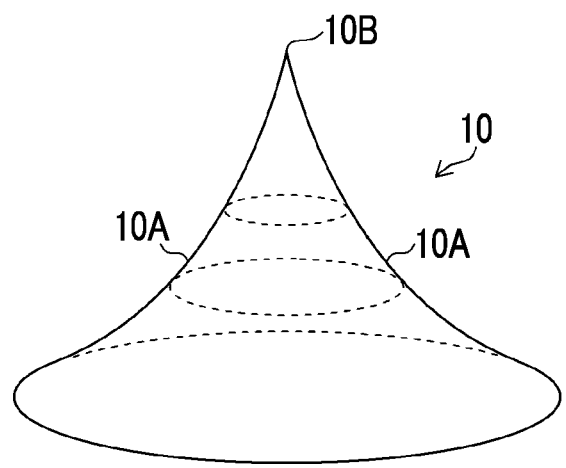
FIG. 3 is a perspective view showing a conical microneedle (needle-like protruding portion) of a transdermal absorption sheet for medical use.
Figure 4:
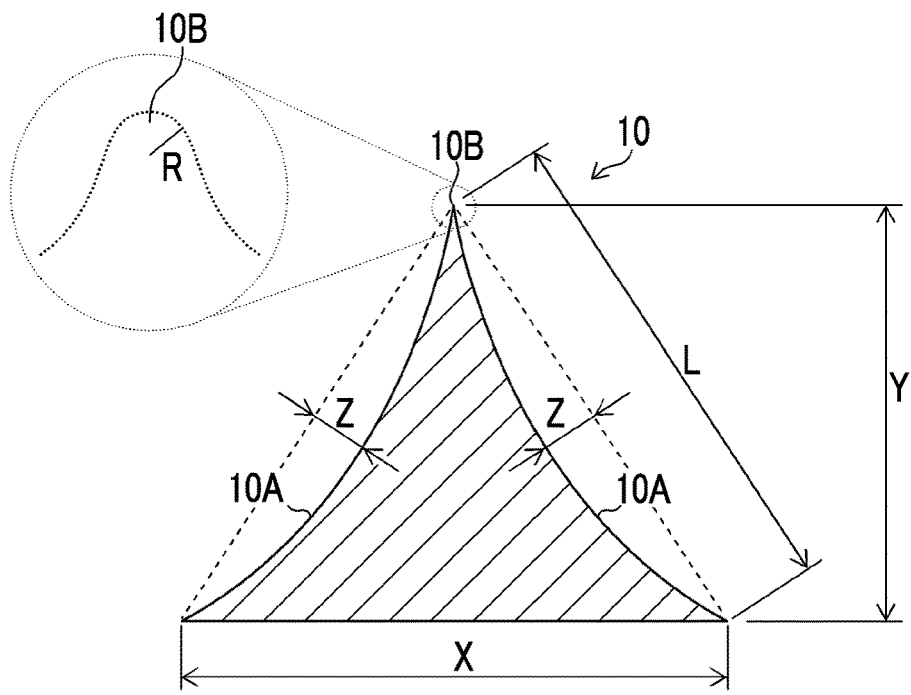
FIG. 4 is a cross-sectional view showing the conical microneedle (needle-like protruding portion) of the transdermal absorption sheet for medical use.

FIGS. 1 and 2 show the quadrangular pyramidal microneedle 10. However, it is preferable that a conical microneedle shown in FIGS. 3 and 4 and pyramidal microneedles of other triangular pyramid shapes have the same size. In a case of the conical shape, the diameter X of the bottom surface is preferably in a range of 0.1 μm or more and 1,000 μm or less, and more preferably in a range of 50 μm or more and 500 μm or less. In addition, in a case in which the length of a segment connecting a start point and an end point of the generatrix of the conical surface is represented as L, the maximum depth Z of the curve of the conical surface is preferably 0.04×L or more and 0.2×L or less.

As described above, transdermal absorption sheet for medical use forms a protruding portion array in which the microneedles are arranged in a two-dimensional array. In order to allow the microneedle to be easily stuck into the surface of the skin, it is important to sufficiently sharpen the microneedle tip end 10B. The radius of the curvature R of the microneedle tip end 10B is preferably 20 μm or less. In order to form a microneedle 10 having a tip end with a radius of curvature R of 20 μm or less, an important point is whether a solution of a polymer resin can be injected down to the tip end (bottom) of a needle-like recessed portion corresponding to an inverted shape of the protruding portion array to be formed in the mold (form) to allow accurate transfer.

In addition, the transdermal absorption sheet for medical use needs to contain a drug, but many drugs are expensive. Thus, it is important to contain a drug in the transdermal absorption sheet such that the drug is concentrated at the portion of each microneedle and to fill the transdermal absorption sheet with the drug with high accuracy in terms of costs.

Method of Producing Transdermal Absorption Sheet for Medical Use

Next, the method of producing the transdermal absorption sheet for medical use according to the embodiment of the present invention will be described.

Production of Mold

Figure 5:
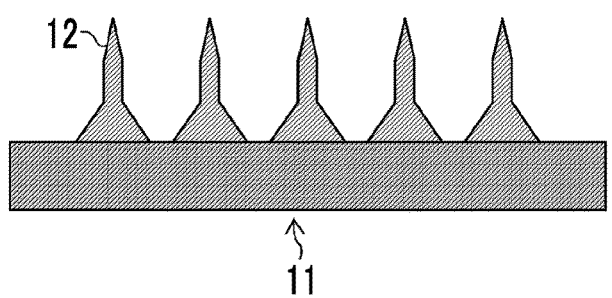
FIG. 5 is a step diagram of a method of producing a mold.
Figure 6:
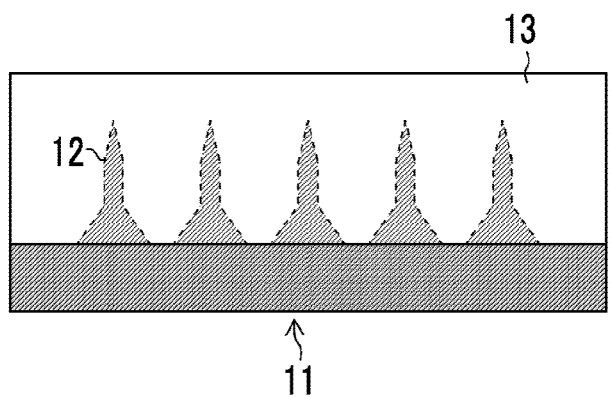
FIG. 6 is a step diagram of the method of producing the mold.
Figure 7:
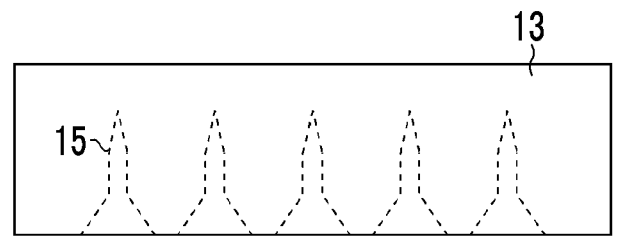
FIG. 7 is a step diagram of the method of producing the mold.

FIGS. 5 to 7 are step diagrams illustrating the production of a mold (form).

As shown in FIG. 5, an original plate which is used for producing a mold for producing the transdermal absorption sheet for medical use is first produced.

Two kinds of methods for producing an original plate 11 are available. A first method is a method of applying a photo resist to a Si substrate and then exposing and developing the photo resist. Then, etching such as reactive ion etching (RIE) is performed on the photo resist to produce an array of conical shape portions (needle-like protruding portions) 12 on a surface of the original plate 11. In a case in which etching such as RIE is performed so as to form the conical shape portions on the surface of the original plate 11, the conical shapes can be formed by carrying out etching in an oblique direction while the Si substrate is being rotated.

The second method is a method of machining a metal substrate such as Ni using a cutting tool such as a diamond bit to form an array of the shape portions 12 shaped like quadrangular pyramids or the like on the surface of the original plate 11.

Next, the mold is produced. Specifically, as shown in FIG. 6, the mold 13 is produced from the original plate 11. Since the original plate 11 has the shape of cones or pyramids (such as quadrangular pyramids) with pointed tip ends, the following methods are conceived which enables to precisely transfer the shape of the original plate 11 to the mold 13 and then to peel off the mold 13 from the original plate 11, while producing the mold 13 at a low cost.

The first method is a method of pouring, into the original plate 11, a silicone resin containing polydimethylsiloxane (PDMS, for example, SYLGARD 184, manufactured by Dow Corning Toray Co., Ltd.) with a curing agent added thereto, heating and curing the silicone resin at 100° C., and then peeling off the silicone resin from the original plate 11. The second method is a method of pouring, into the original plate 11, a UV (ultraviolet) curable resin that is curable by irradiation with ultraviolet light, irradiating the UV curable resin with ultraviolet light in a nitrogen atmosphere, and then peeling off the UV curable resin from the original plate 11. The third method is a method of pouring a solution of a plastic resin such as polystyrene or polymethylmethacrylate (PMMA) dissolved in an organic solvent, into the original plate 11 coated with a release agent, volatilizing the organic solvent by drying to cure the plastic resin, and then peeling off the plastic resin from the original plate 11.

Accordingly, the mold 13 in which needle-like recessed portions 15 that are inverted shapes of cones or pyramids on the original plate 11 are arranged in a two-dimensional array is produced. The mold 13 produced as described above is shown in FIG. 7. In addition, the mold 13 can be easily produced any number of times using any of the above-described methods.

Figure 8:
FIG. 8 is a cross-sectional view showing a mold provided with a frame.
Figure 9:
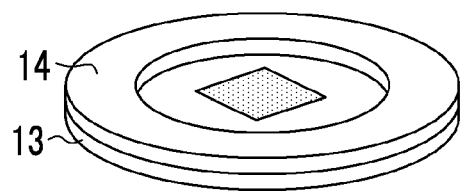
FIG. 9 is a perspective view showing the mold provided with the frame.

FIGS. 8 and 9 are views in which a frame 14 is provided. FIG. 8 is a cross-sectional view showing a mold provided with a frame in the vicinity thereof and FIG. 9 is a perspective view showing the mold shown in FIG. 8. Provision of the frame 14 allows a solution of a polymer resin (hereinafter, also referred to as a "base liquid"), which is a material for the sheet portion to be prevented from flowing out from the mold 13 in a case in which the transdermal absorption sheet for medical use is formed to have a desired film thickness.

At this time, a step between the mold 13 and the frame 14 is preferably 50 μm or more and 10 mm or less. Furthermore, the form in FIGS. 8 and 9 is configured to enable the mold 13 and the frame 14 to be separated from each other, but the mold 13 and the frame 14 may be integrated together. In a case in which the mold and the frame are configured to be separable, the frame 14 can be removed in a drying step and a peeling-off step.

Figure 10:
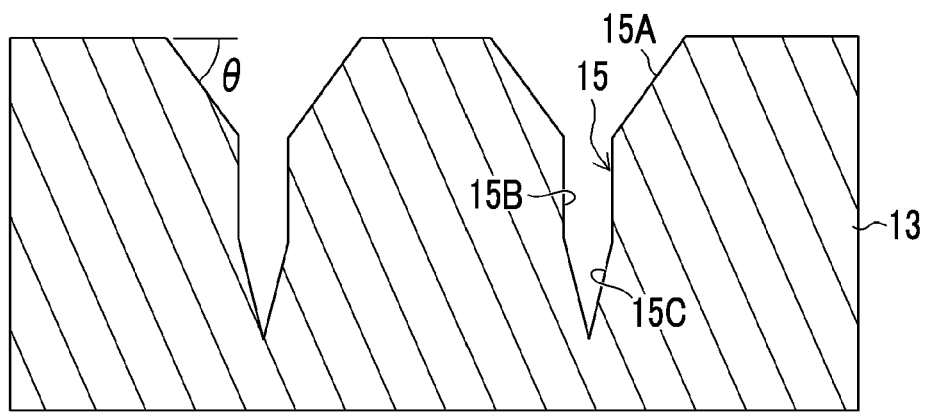
FIG. 10 is a cross-sectional view showing an embodiment of another mold.

FIG. 10 shows another preferable embodiment of the mold 13. The needle-like recessed portion 15 includes a tapered inlet portion 15A that is narrower in a depth direction from the surface of the mold 13, an intermediate recessed portion 15B with a constant width in the depth direction, and a tip end recessed portion 15C that is tapered in the depth direction. The angle θ of the taper is preferably within the range of 10° to 20°. The tapered inlet portion 15A allows the needle-like recessed portion 15 to be easily filled with the polymer solution.

Figure 11:
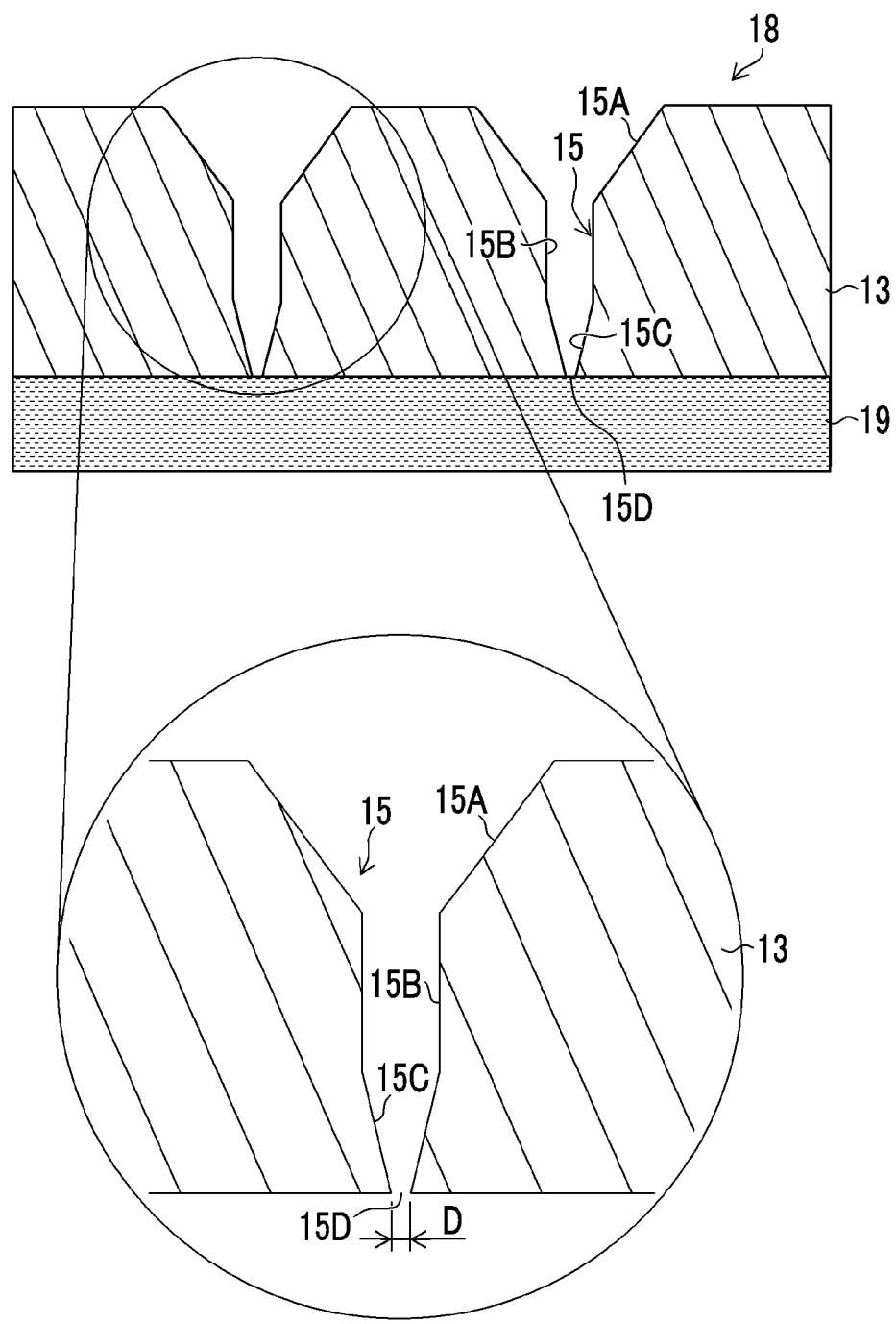
FIG. 11 is a cross-sectional view showing an embodiment of a mold complex.

FIG. 11 shows an embodiment of a mold complex 18 that is more preferable in production of the transdermal absorption sheet for medical use.

As shown in FIG. 11, the mold complex 18 includes the mold 13 in which an air vent hole 15D is formed at the tip end (bottom) of each needle-like recessed portion 15 and a gas permeable sheet 19 laminated to a back surface of the mold 13 and formed of a material that allows gas to permeate, while preventing liquid from permeating. The air vent hole 15D is formed as a through-hole that penetrates the back surface side of the mold 13. In this regard, the back surface of the mold 13 refers to a surface on the side of the mold 13 on which the air vent hole 15D is formed. Thus, a tip end of the needle-like recessed portion 15 communicates with the atmosphere via the air vent hole 15D and the gas permeable sheet 19.

The use of the mold complex 18 as described above allows only the air present in the needle-like recessed portions 15 to be driven out from the needle-like recessed portions 15 while preventing permeation of the transdermal absorption material solution, which is the material or the transdermal absorption sheet for medical use and fills the needle-like recessed portions 15. This improves transferability with which the shape of the needle-like recessed portions 15 is transferred to the transdermal-absorption material and allows formation of sharper microneedles 10.

The diameter D (diameter) of the air vent hole 15D is preferably within the range of 1 to 50 μm. By setting the diameter D of the air vent hole 15D to be within the above range, while the air vent hole is allowed to sufficiently accomplish the functions thereof, the sharpness of the tip end portion of the molded microneedle 10 can be maintained.

As a gas permeable sheet 19 formed of a material that allows gas to permeate while preventing liquid from permeating, for example, latex (manufactured by Asahi Kasei Chemicals Corporation) may be suitably used.

As the material used for the mold 13, an elastic raw material and a metallic raw material can be used. Of these, an elastic raw material is preferable and a raw material with high gas permeability is more preferable. The oxygen permeability, which is representative of the gas permeability, is preferably more than $1 \times 10^{-12}$ (mL/s·m·Pa) and more preferably more than $1 \times 10^{-10}$ (mL/s·m·Pa). Setting the gas permeability to within the above range allows the air present in the needle-like recessed portions 15 in the mold 13 to be driven out from the mold 13 side. Thus, a transdermal absorption sheet for medical use with few defects can be produced. Specifically, examples of such materials include materials obtained by melting a silicone resin (for example, SYLGARD 184 or 1310ST), a UV curable resin, or a plastic resin (for example, polystyrene or polymethylmethacrylate (PMMA)), and materials obtained by dissolving any of above resins into a solvent. Among these materials, silicone rubber-based raw materials can be suitably used due to the durability thereof against transfers using repeated pressurization and the good peelability thereof from the raw material. Furthermore, examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX material), and alloys thereof.

Polymer Solution

The polymer solution that is a solution of the polymer resin which becomes a material for the transdermal absorption sheet for medical use used for the present embodiment will be described. There are two kinds of polymer solutions of a drug-containing solution containing a drug in a liquid (corresponding to the drug solution), and a non-drug-containing base liquid which mainly becomes a material for the sheet portion of the transdermal absorption sheet for medical use.

It is preferable that a biocompatible resin is used as the raw material for the resin polymer used for the polymer solution. It is preferable to use, as such a resin, sugars such as glucose, maltose, pullulan, dextran, sodium chondroitin sulfate, sodium hyaluronate, hydroxypropyl cellulose, and hydroxyethyl starch, protein such as gelatin, polylactic acid, or biodegradable polymers such as polylactic acid and a lactic acid-glycollic acid copolymer. Among these, sodium chondroitin sulfate, hydroxypropyl cellulose, and dextran can be suitably used. In addition, gelatin-based raw materials have adhesiveness with many base materials and have a high gel strength as materials to be gelated. Therefore, the gelatin-based materials can be used during a peeling-off step described below because the materials can be brought into tight contact with the base material to allow the polymer sheet to be peeled off from the mold using the base material. Although the concentration varies depending on the material, it is preferable to be such a concentration that 10% to 50% by weight of the resin polymer is contained in the solution. Additionally, a solvent used for dissolution may be other than warm water as long as the solvent has volatility, and methylethylketone (MEK), alcohol, or the like may be used. A drug to be fed to the inside of the human body may concurrently be dissolved into the solution of the polymer resin according to the application.

For a method for preparing the polymer solution, in a case in which a water-soluble polymer (gelatin or the like) is used, the solution can be produced by dissolving water-soluble powder into water and adding a chemical to the solution. In a case in which the material is difficult to dissolve into water, the material may be dissolved on heating. The temperature can be appropriately selected depending on the type of the polymer material, but heating is preferably performed at a temperature of about 60° C. or lower. Furthermore, in a case in which a thermally melted polymer (maltose or the like) is used, the solution can be produced by dissolving the raw material and the chemical on heating. The heating temperature is preferably a temperature at which the raw material is melted, and is specifically about 150° C.

The viscosity of the solution of the polymer resin is preferably 2,000 Pa·s or less and more preferably 1,000 Pa·s or less. Appropriate adjustment of the viscosity of the solution of the polymer resin facilitates injection of the solution into the recessed portions of the mold. In addition, the viscosity of the drug-containing solution is preferably 100 Pa·s or less and more preferably 10 Pa·s or less.

Drug

The drug is not limited as long as the drug has the functions of a drug. In particular, the drug is preferably selected from the group consisting of peptide, protein, nucleic acid, polysaccharide, a vaccine, and a medical compound belonging to a water-soluble low-molecular-weight compound. As the water-soluble polymer substance contained in the drug-containing layer, one that does not interact with the drug contained in the layer is preferably used. For example, in a case in which protein is used as the drug and a chargeable polymer substance is mixed with the protein, the protein and the polymer substance electrostatically interact with each other to form an aggregate, which is aggregated and precipitated. Therefore, in a case in which a chargeable substance is used in the drug, a water-soluble polymer substance with no charge such as hydroxyethyl starch or dextran is preferably used.

Production of Transdermal Absorption Sheet for Medical Use

A method for producing the transdermal absorption sheet for medical use using the mold 13 produced as described above will be described.

Drug Solution Filling Step

Figure 12:
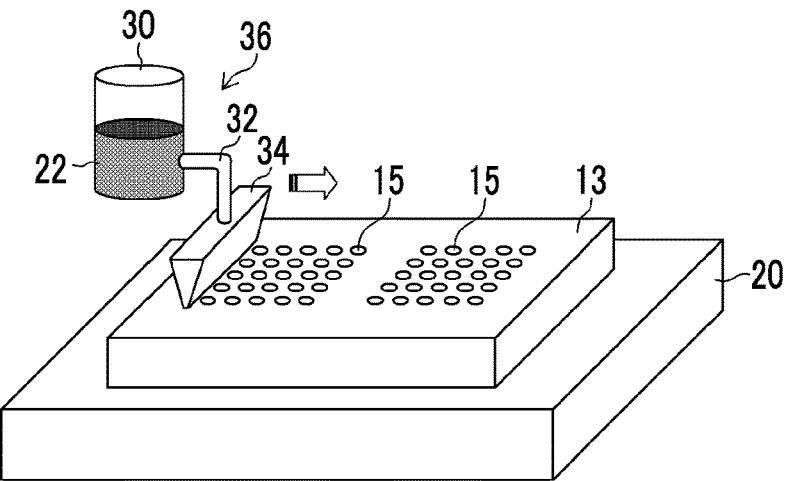
FIG. 12 is a schematic view showing a drug solution filling step.
Figure 13:
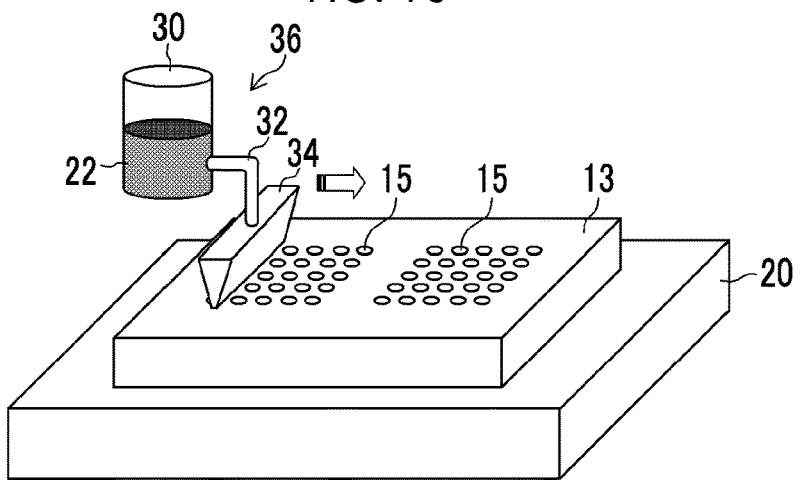
FIG. 13 is a schematic view showing the drug solution filling step.
Figure 14:
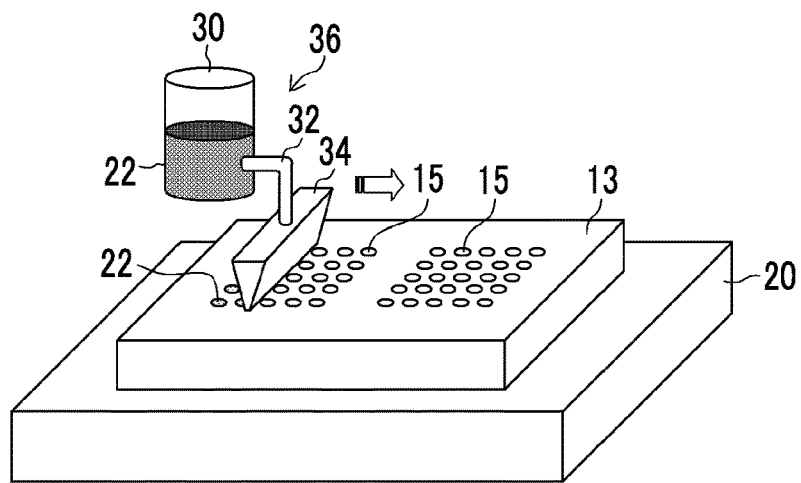
FIG. 14 is a schematic view showing the drug solution filling step.

FIGS. 12 to 14 are views showing a drug solution filling step. As shown in FIG. 12, first, the mold 13 with the two-dimensionally arranged needle-like recessed portions 15 is arranged on a base 20. Two sets of a plurality of needle-like recessed portions 15, each set including 5×5 two-dimensionally arranged needle-like recessed portions 15, are formed in the mold 13. A liquid feeding apparatus 36 is prepared which has a tank 30 which houses a drug-containing solution 22, a pipe 32 which is connected to the tank, and a nozzle 34 which is connected to the tip end of the pipe 32.

Figure 15:
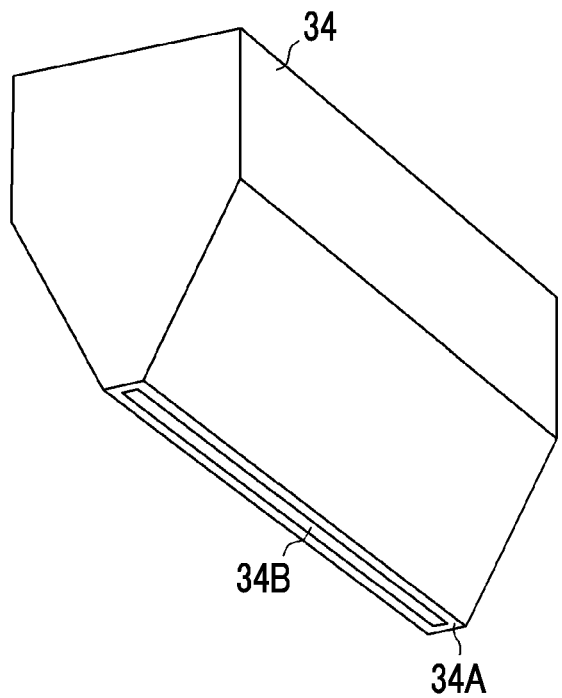
FIG. 15 is a perspective view showing a tip end portion of a nozzle.

FIG. 15 is a schematic perspective view showing the tip end portion of the nozzle. As shown in FIG. 15, the tip end of the nozzle 34 includes a lip portion 34A which is a flat surface and a slit-shaped opening portion 34B. The slit-shaped opening portion 34B, for example, allows a plurality of needle-like recessed portions 15 constituting one line to be simultaneously filled with the drug-containing solution 22. The size (length and width) of the opening portion 34B is selected as needed according to the number of needle-like recessed portions 15 to be filled at a time.

An increase in the length of the opening portion 34B allows an increased number of needle-like recessed portions 15 to be filled with the drug-containing solution 22 at a time. Thus, productivity can be improved.

Figure 16:
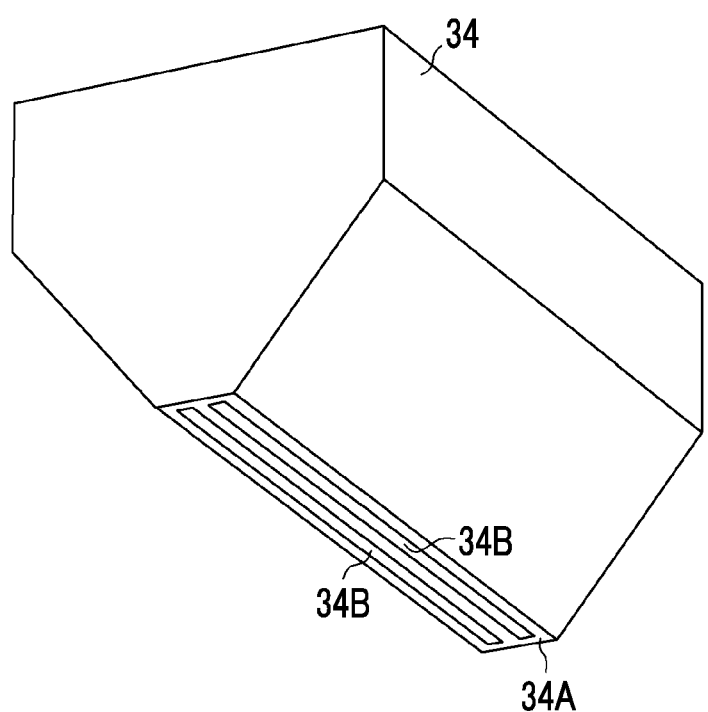
FIG. 16 is a perspective view showing a tip end portion of another nozzle.

FIG. 16 is a schematic perspective view of a tip end portion of another nozzle. As shown in FIG. 16, the lip portion 34A at the tip end of the nozzle 34 has two slit-shaped opening portions 34B. By the two opening portions 34B, for example, the plurality of needle-like recessed portions 15 constituting two lines can be simultaneously filled with the drug-containing solution 22.

As a material used for the nozzle 34, an elastic raw material and a metallic raw material can be used. For example, Teflon (registered trademark), stainless steel, or titanium may be used.

A drug solution filling step will be described with reference to FIG. 13. As shown in FIG. 13, the position of the opening portion 34B in the nozzle 34 is adjusted over the needle-like recessed portions 15. The lip portion 34A of the nozzle 34 is in contact with the surface of the mold 13. The drug-containing solution 22 is fed from the liquid feeding apparatus 36 to the mold 13, and the needle-like recessed portions 15 are filled with the drug-containing solution 22 through the opening portion 34B in the nozzle 34. In the embodiment, a plurality of needle-like recessed portions 15 constituting one line are simultaneously filled with the drug-containing solution 22. However, the present invention is not limited to this configuration. The needle-like recessed portions 15 may be filled with the drug-containing solution 22 one by one. Furthermore, the use of the nozzle 34 shown in FIG. 16 allows a plurality of needle-like recessed portions 15 constituting a plurality of lines to simultaneously fill a plurality of lines with the drug-containing solution 22.

In a case in which the mold 13 is formed of a raw material having gas permeability, the drug-containing solution 22 can be sucked by sucking the back surface of the mold 13, promoting filling of the inside of the needle-like recessed portions 15 with the drug-containing solution 22.

Next, as shown in FIG. 14, with the lip portion 34A of the nozzle 34 and the surface of the mold 13 in contact with each other, the liquid feeding apparatus 36 is relatively moved in a direction perpendicular to a length direction of the opening portion 34B, to move the nozzle 34 to the needle-like recessed portions 15 not filled with the drug-containing solution 22. The position of the opening portion 34B in the nozzle 34 is adjusted over the needle-like recessed portions 15. The embodiment has been described with reference to the example in which the nozzle 34 is moved. However, the mold 13 may be moved.

Since the nozzle 34 is moved with the lip portion 34A of the nozzle 34 and the surface of the mold 13 in contact with each other, the nozzle 34 can scrape off the drug-containing solution 22 remaining on the surface of the mold 13 except on the needle-like recessed portions 15. Then, the drug-containing solution 22 can be prevented from remaining on the mold 13 except on the needle-like recessed portions 15.

The filling of the drug-containing solution 22 in FIG. 13 and the movement of the nozzle 34 in FIG. 14 are repeated to fill the 5×5 two-dimensionally arranged needle-like recessed portions 15 with the drug-containing solution 22. In a case in which the 5×5 two-dimensionally arranged needle-like recessed portions 15 are filled with the drug-containing solution 22, the liquid feeding apparatus 36 is moved to the adjacent 5×5 two-dimensionally arranged needle-like recessed portions 15, and the filling of the drug-containing solution 22 in FIG. 13 and the movement of the nozzle 34 in FIG. 14 are repeated. The adjacent 5×5 two-dimensionally arranged needle-like recessed portions 15 are also filled with the drug-containing solution 22.

The above-described filling of the drug-containing solution 22 and the movement of the nozzle 34 may be in (1) a form in which the needle-like recessed portions 15 are filled with the drug-containing solution 22 while the nozzle 34 is being moved or (2) a form in which, while the nozzle 34 is in motion, the nozzle 34 is temporarily stopped over the needle-like recessed portions 15 to fill the needle-like recessed portions 15 with the drug-containing solution 22, and the nozzle 34 is moved again after the filling. Between the filling of the drug-containing solution 22 and the movement of the nozzle 34, the lip portion 34A of the nozzle 34 is in contact with the surface of the mold 13.

Figure 17:
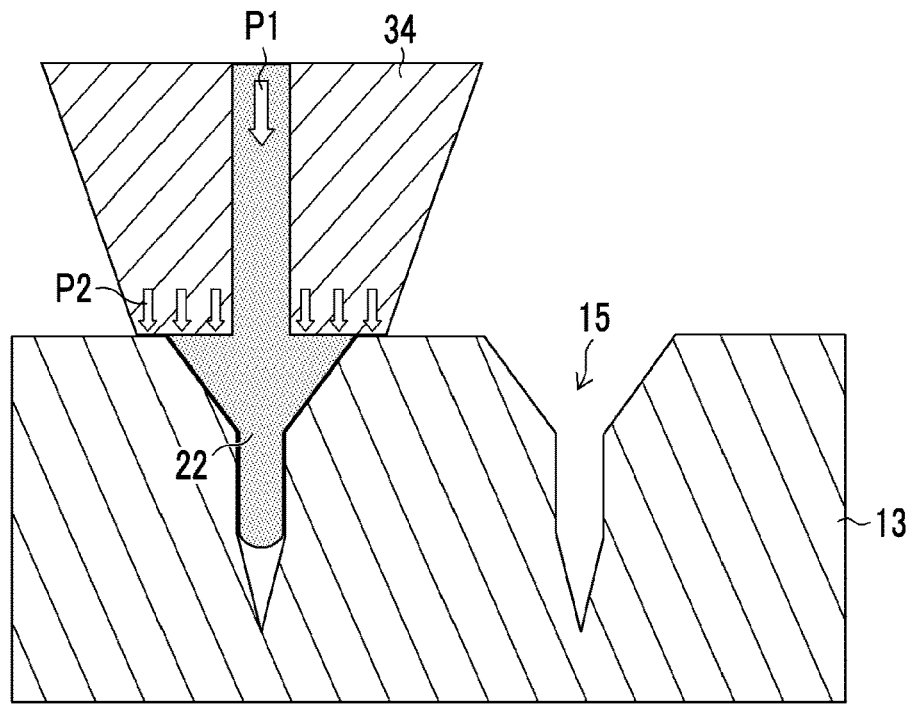
FIG. 17 is a partially enlarged view showing the mold and the tip end of the nozzle while filling.

FIG. 17 is a partially enlarged view of the tip end of the nozzle 34 and the mold 13 during filling of the needle-like recessed portions 15 with the drug-containing solution 22. As depicted in FIG. 17, filling of the inside of the needle-like recessed portions 15 with the drug-containing solution 22 can be promoted by applying a pressuring force P1 into the nozzle 34. Further, in a case in which the inside of the needle-like recessed portions 15 is filled with the drug-containing solution 22, a pressing force P2 with which the nozzle 34 is brought into contact with the surface of the mold 13 is preferably set equal to or greater than the pressuring force P1 in the nozzle 34. Setting the pressing force P2 the pressuring force P1 enables the drug-containing solution 22 to be restrained from leaking from the needle-like recessed portions 15 to the surface of the mold 13.

Figure 18:
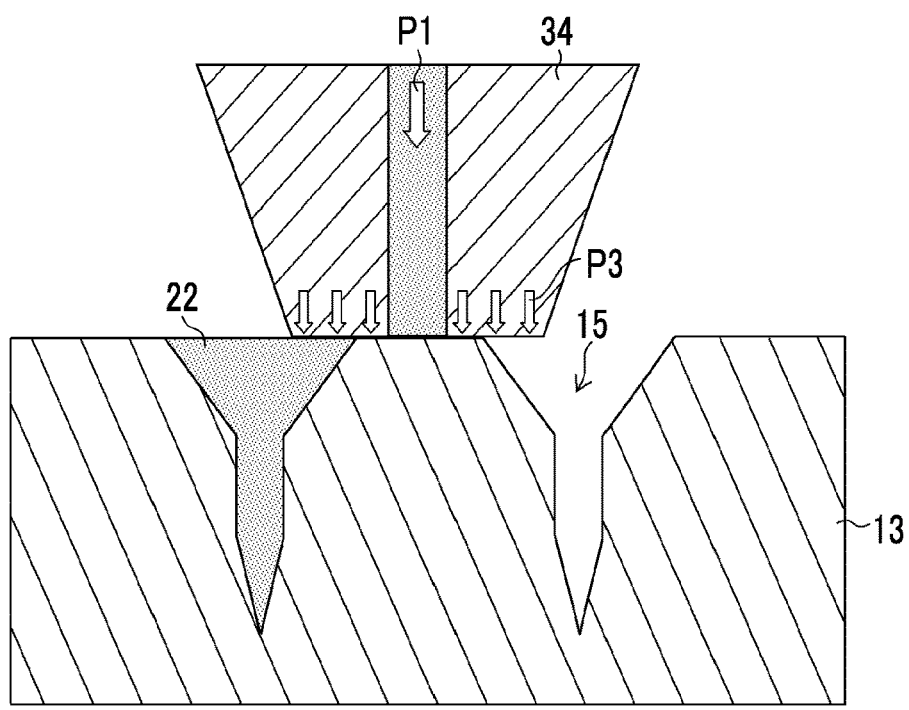
FIG. 18 is a partially enlarged view showing the mold and the tip end of the nozzle while moving.

FIG. 18 is a partially enlarged view of the tip end of the nozzle 34 and the mold 13 during movement of the nozzle 34. In a case in which the nozzle 34 is moved relative to the mold 13, a pressing force P3 with which the nozzle 34 is brought into contact with the surface of the mold 13 is preferably set to be weaker than the pressing force P2 with which the nozzle 34 is brought into contact with the surface of the mold 13 while the filling is performed. This is intended to reduce damage to the mold 13 and to suppress deformation of the mold 13 accompanied by compression.

Figure 19:
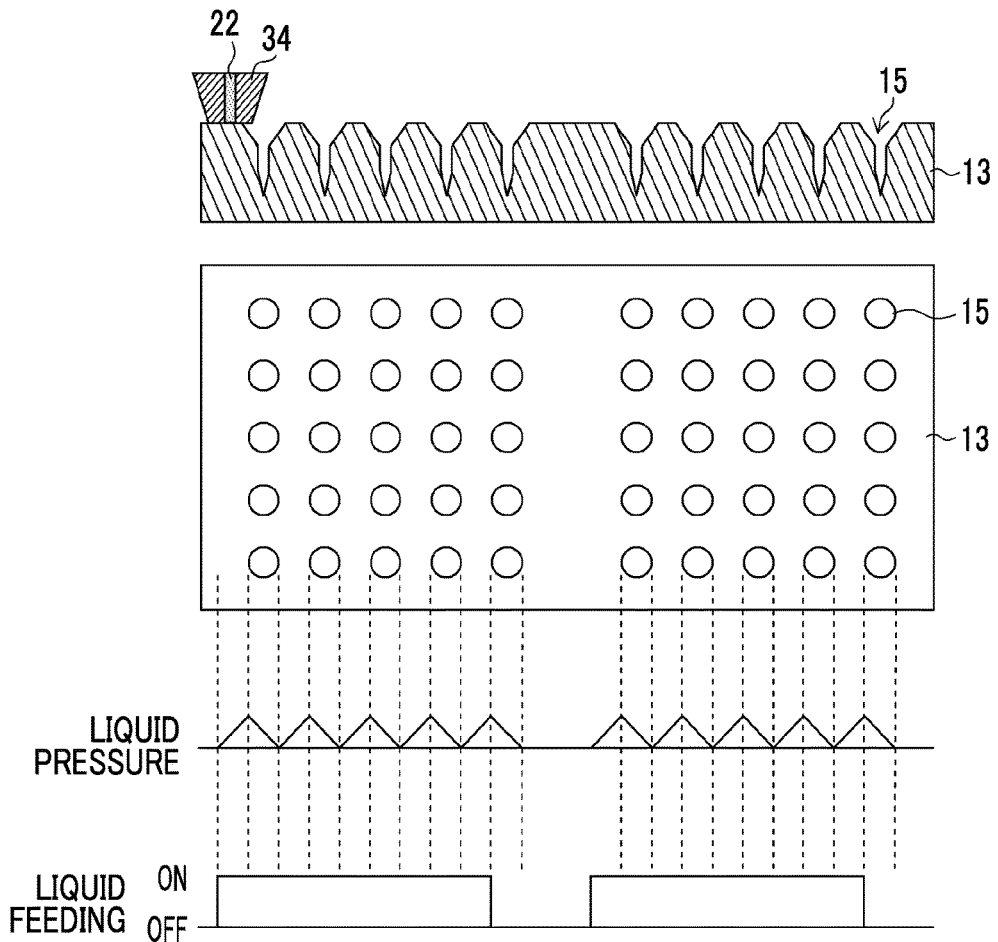
FIG. 19 is a diagram illustrating the relationship between the liquid pressure in the nozzle and feeding of the drug-containing solution.

FIG. 19 is a diagram illustrating the relationship between the liquid pressure in the nozzle and feeding of the drug-containing solution. As shown in FIG. 19, feeding of the drug-containing solution 22 is started before the nozzle 34 is positioned over the needle-like recessed portions 15. This is because the needle-like recessed portions 15 are reliably filled with the drug-containing solution 22. The drug-containing solution 22 is continuously fed to the mold 13 until the filling of the plurality of needle-like recessed portions 15 constituted of the 5×5 needle-like recessed portions 15 is complete. The feeding of the drug-containing solution 22 to the mold 13 is stopped before the nozzle 34 is positioned over the fifth line of the needle-like recessed portions 15. This allows the drug-containing solution 22 to be prevented from overflowing the needle-like recessed portions 15. In a case in which the feeding of the drug-containing solution 22 is started, the liquid pressure in the nozzle 34 is increased in areas in which the nozzle 34 is not positioned over the needle-like recessed portions 15. On the other hand, in a case in which the nozzle 34 is positioned over the needle-like recessed portions 15, the needle-like recessed portions 15 are filled with the drug-containing solution 22 to lower the liquid pressure in the nozzle 34. The variation in liquid pressure is repeated.

In case in which the filling of the plurality of needle-like recessed portions 15 constituted of the 5×5 needle-like recessed portions 15 is complete, the nozzle 34 is moved to the adjacent plurality of needle-like recessed portions 15 constituted of the 5×5 needle-like recessed portions 15. Regarding the liquid feeding, the feeding of the drug-containing solution 22 is preferably stopped at the time of movement to the adjacent plurality of needle-like recessed portions 15 constituted of the 5×5 needle-like recessed portions 15. Along distance is present between the fifth line of needle-like recessed portions 15 and the next first line of needle-like recessed portions 15. In a case in which the drug-containing solution 22 is continuously fed while the nozzle 34 is moving between the fifth line of needle-like recessed portions 15 and the next first line of needle-like recessed portions 15, the liquid pressure in the nozzle 34 may be excessively high. As a result, the drug-containing solution 22 may flow out from the nozzle 34 onto an area other than the needle-like recessed portions 15 in the mold 13. In order to suppress this, it is preferable that the feeding of the drug-containing solution 22 is stopped.

In a case in which the filling of the needle-like recessed portions 15 with the drug-containing solution 22 is complete, the process proceeds to a step of forming a polymer sheet with needle-like protruding portions each formed on a surface of the sheet, the polymer sheet including a drug-containing layer formed of the drug-containing solution 22 and a non-drug-containing layer formed of a non-drug-containing solution. The needle-like protruding portions have inverted shapes of the needle-like recessed portions.

The above-described drug solution filling step is carried out by pressing the tip end of the nozzle 34 against the mold 13 and pressurizing the inside of the nozzle 34. However, the drug solution filling step is not limited to this method. For example, the needle-like recessed portions can be filled with the drug-containing solution by feeding the drug-containing solution to the mold by a nozzle, a dispenser, or the like, and moving a blade while being brought into contact with the surface of the mold.

After the drug solution filling step, a base liquid feeding step and a drying step are carried out. Regarding the drying step, several aspects will be described.

First Embodiment

Drug Drying Step

Figure 20:
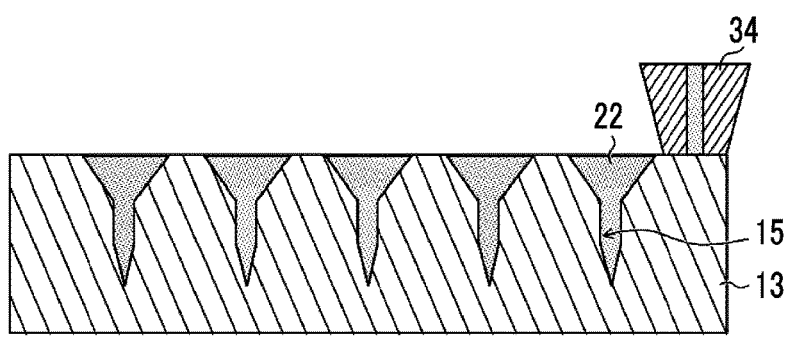
FIG. 20 is a diagram illustrating a step of forming a polymer sheet.

In a first embodiment, after a drug feeding step, a drug drying step is carried out to dry the drug. FIG. 20 is a diagram illustrating a state after the needle-like recessed portions 15 of the mold 13 are filled with the drug-containing solution 22. For the filling method, the filling can be carried out by bringing the tip end portion of the nozzle into contact with the mold as shown in FIGS. 12 to 14.

Figure 21:
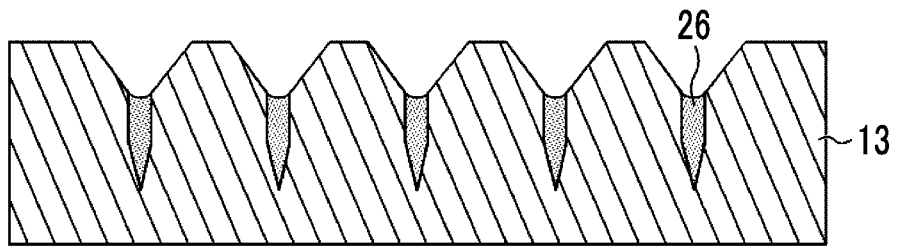
FIG. 21 is a diagram illustrating the step of forming the polymer sheet.

Next, as shown in FIG. 21, the drug-containing solution 22 filling the inside of the needle-like recessed portions 15 is dried and solidified to form a drug-containing layer 26 in the in each of the needle-like recessed portions 15. In a case in which the drug-containing solution 22 is dried and solidified, the tip end of the needle-like recessed portion 15 can be filled with the drug-containing solution 22 by the reduced pressure suction from the back surface of the mold 13.

The method of drying the drug-containing solution 22 is not particularly limited. For example, drying can be carried out by drying by natural drying, heating, and dry air supply.

Sterile Filtration Step

Next, sterile filtration is carried out by a sterile filtration step for preparation for feeing the base liquid 24. In the embodiment, since the base liquid is used as the material for the transdermal absorption sheet for medical use, the base liquid 24 is subjected to sterile filtration. Regarding the method for sterile filtration, it is possible to remove unwanted materials from the base liquid by using a hollow fiber membrane, a reverse osmosis membrane, a membrane filter or the like. In the present invention, although there is no particular limitation, the base liquid is preferably filtered by means of a filter having a sterile pore size (preferably a 0.2 μm sterile filter).

Base Liquid Feeding Step

Figure 22:
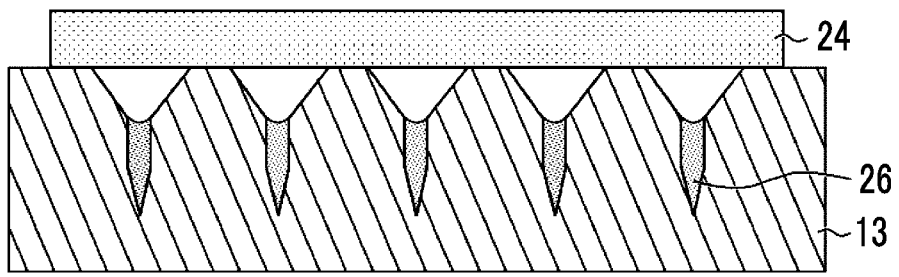
FIG. 22 is a diagram illustrating the step of forming the polymer sheet.

Next, as shown in FIG. 22, the base liquid 24, which has been subjected to sterile filtration, is fed to the surface of the mold 13 on which the drug-containing layer 26 is formed. The feeding of the base liquid can be carried out by applying the base liquid using a dispenser. In addition, in addition to the application of the base liquid using a dispenser, bar coating, spin coating, and an application using a spray or the like are applicable. Since the drug-containing layer 26 is formed by drying and solidifying the drug-containing solution 22 and then base liquid 24 is fed as in the embodiment, the drug in the drug-containing layer 26 can be prevented from diffusing to the base liquid 24.

Drying Step (Base Liquid Drying Step)

Figure 23:
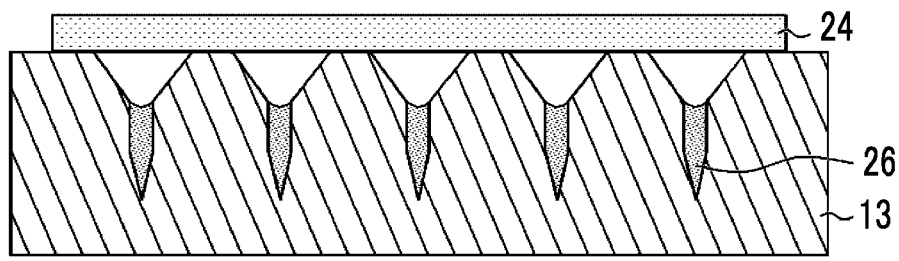
FIG. 23 is a diagram illustrating the step of forming the polymer sheet.

Next, as shown in FIG. 23, the base liquid fed to the mold 13 is dried. For the drying method, drying can be carried out in the same method as the drying method of the drug-containing solution 22. In the embodiment, since the drug-containing layer 26 is formed by the drug drying step, a space is formed on the opening portion side of the needle-like recessed portion 15, that is, between the drug-containing layer 26 and the base liquid 24 by the contraction caused by evaporating and drying moisture from the drug-containing solution. The base liquid 24 is dried from the surface side of the mold 13. However, by providing a space in the needle-like recessed portion 15, the base liquid can be also dried from the space. Thus, drying of the base liquid 24 can be promoted.

Base Liquid Moving Step

Figure 24:
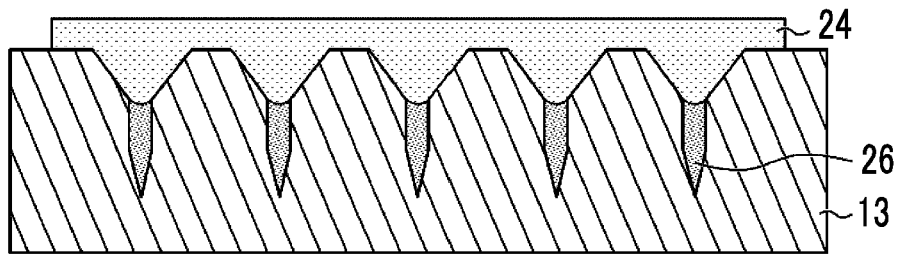
FIG. 24 is a diagram illustrating the step of forming the polymer sheet.

During the base liquid drying step, as shown in FIG. 24, a base liquid moving step of moving the base liquid 24 to the inside of the needle-like recessed portion 15 is carried out. The base liquid moving step can be carried out by sucking the base liquid from the opposite side of the surface of the mold 13 on which the needle-like recessed portions 15 are formed. In addition, the base liquid moving step can be carried out by pressurizing the base liquid 24 from the surface side of the mold 13 on which the needle-like recessed portions 15 are formed.

The suction can be carried out from the opposite side of the surface of the mold 13 on which the needle-like recessed portions 15 are formed in such a manner that the mold 13 is arranged in a suction apparatus and suction is carried out from the opposite side of the surface of the mold 13 on which the needle-like recessed portions 15 are formed. For the method of carrying out pressurization from the surface side of the mold 13 in which the needle-like recessed portions 15 are formed, pressurization only from the surface side of the mold 13 can be carried out by providing a frame around the mold 13 and putting the mold in a container that can apply pressure, such as a pressurizing container, to apply pressure.

The base liquid moving step is carried out after the average concentration of the solid contents of the base liquid is increased by 5% by weight or more from the average concentration of the solid contents of the base liquid when the base liquid is fed to the mold 13. By carrying out the base liquid moving step after the base liquid is dried on the surface of the mold 13, the drying time of the base liquid can be reduced. In a case in which the base liquid 24 is moved into the needle-like recessed portion 15 and then dried, the base liquid 24 is in a sealed state in the needle-like recessed portion 15 and the base liquid is not easily dried. Thus, it takes a long time for drying. By drying the base liquid 24 on the surface of the mold 13, the base liquid can be easily dried and the drying time can be reduced.

In addition, the base liquid moving step is carried out in a state in which the average concentration of the solid contents of the base liquid is 75% by weight or less. In a case in which the average concentration of solid contents is more than 75% by weight, the viscosity of the base liquid is increased and the base liquid is not easily moved into the needle-like recessed portion 15. Thus, the base liquid moving step is carried out in a state in which the average concentration of the solid contents is 75% by weight or less.

The average concentration of the solid contents of the base liquid in a case in which the base liquid moving step is carried out is increased by 5% by weight or more, preferably 15% by weight or more, and more preferably 30% by weight or more, from the average concentration of the solid contents of the base liquid in the case of the base liquid feeding step, and then the base liquid moving step is carried out. In a case in which the base liquid is dried before the base liquid moving step, the drying time can be further reduced. However, the concentration range is set such that the average concentration of solid contents is not more than 75% by weight. The average concentration of the solid contents of the base liquid 24 can be obtained from a change in weight by measuring the change in weight before and after drying.

Figure 25:
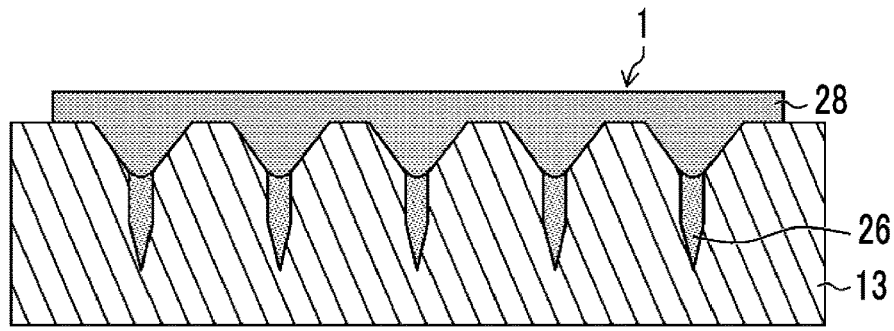
FIG. 25 is a diagram illustrating the step of forming the polymer sheet.

After the base liquid 24 is moved into the needle-like recessed portion 15, as shown in FIG. 25, the drying is further carried out and thus a polymer sheet 1 including the drug-containing layer 26 and a non-drug-containing layer 28. The suction or pressurization for moving the base liquid 24 to the inside of the needle-like recessed portion 15 is stopped after it is confirmed that the needle-like recessed portion 15 can be filled with the base liquid 24 without mixing of bubbles. Whether bubbles are present or not can be confirmed by using a magnifier, a microscope, or the like. Normally, the needle-like recessed portion 15 can be filled with the base liquid 24 by carrying out the base liquid moving step for about several minutes to 10 minutes.

Peeling-Off Step

After the polymer sheet 1 on which the needle-like protruding portions are formed on the surface is formed, the process proceeds to a peeling-off step of peeling the polymer sheet 1 off from the mold 13.

Figure 26:
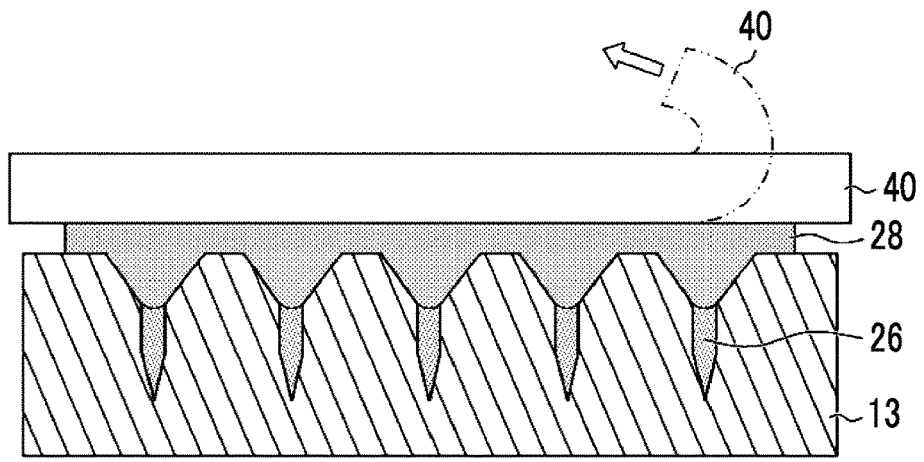
FIG. 26 is a diagram illustrating a peeling-off step.
Figure 27:
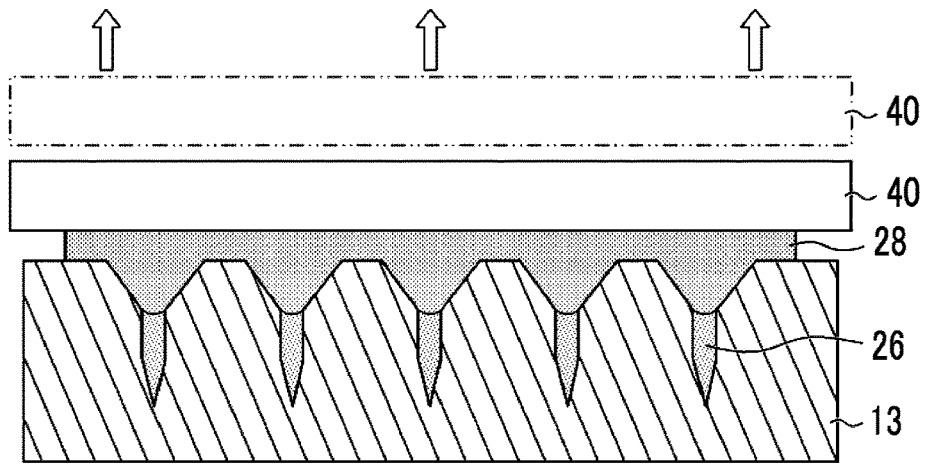
FIG. 27 is a diagram illustrating another peeling-off step.

The method of peeling the polymer sheet 1 off from the mold is not particularly limited. The needle-like protruding portions are desirably prevented from being bent or broken in the case of peeling-off. Specifically, as shown in FIG. 26, a sheet-like substrate 40 on which a pressure sensitive adhesive layer having pressure sensitive adhesiveness is formed is attached onto the polymer sheet 1, and then the polymer sheet 1 can be peeled off by turning the substrate 40 over at the end portion of the polymer sheet 1. However, this method may cause the needle-like protruding portions to be bent. Thus, as shown in FIG. 27, a method may be applied in which suckers (not shown) are installed on the substrate 40 on the polymer sheet 1 and the substrate 40 is then sucked using air and lifted perpendicularly.

Normally, in a case in which a structure with needle-like protruding portions having a high aspect ratio is peeled off from the mold 13 as in the embodiment, high stress is applied due to a large contact area. The needle-like protruding portions that are microneedles may be destroyed and remain in the needle-like recessed portions 15 instead of being peeled off from the mold 13, and a transdermal absorption sheet for medical use produced may be defective. Thus, in the embodiment, the mold 13 is preferably formed of a material that is very easy to peel off. Furthermore, the mold 13 formed of a highly elastic soft material allows relaxation of stress applied to the needle-like protruding portions in the case of peeling-off.

Figure 28:
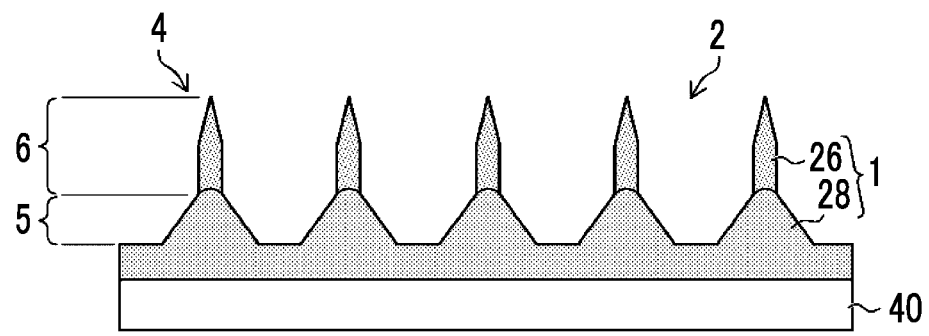
FIG. 28 is a cross-sectional view of a transdermal absorption sheet for medical use.

FIG. 28 shows a transdermal absorption sheet 2 for medical use constituted of the polymer sheet 1 peeled off from the mold 13. The transdermal absorption sheet 2 for medical use is constituted by the substrate 40, the drug-containing layer 26 formed on the substrate 40, and the non-drug-containing layer 28 which does not substantially contain the drug. Needle-like protruding portions 4 on the transdermal absorption sheet 2 for medical use are each constituted of a truncated cone portion 5 and a needle portion 6 on the truncated cone portion 5. The needle portion 6 mainly has a conical or pyramidal needle portion and a cylindrical or rectangular columnar body portion. However, the needle-like protruding portions are not limited to this shape.

Second Embodiment

Next, using FIGS. 29 to 34, a method of producing a transdermal absorption sheet for medical use according to a second embodiment (Drug Drying Step), (Drying Step), and (Base Liquid Moving Step) will be described.

Drug Drying Step

Figure 29:
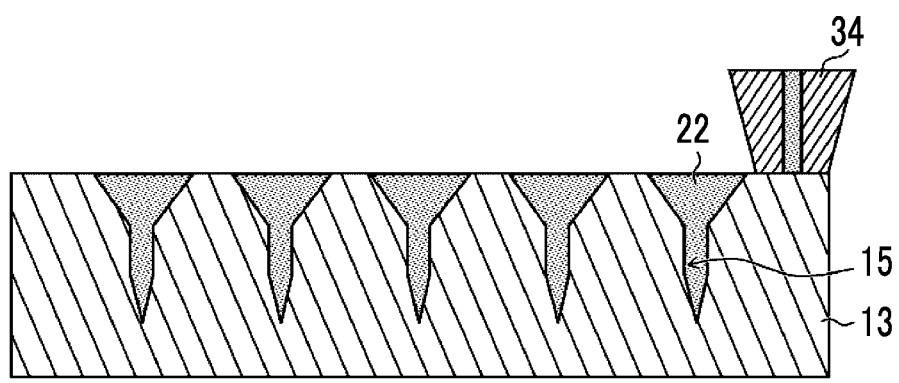
FIG. 29 is a diagram illustrating another step of forming the polymer sheet.
Figure 30:
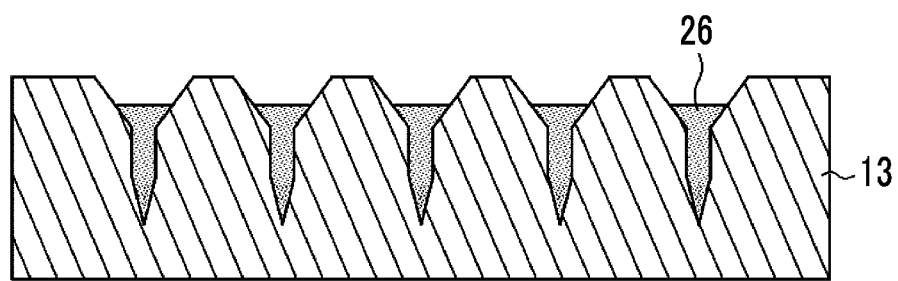
FIG. 30 is a diagram illustrating the other step of forming the polymer sheet.

FIG. 29 is a diagram illustrating a state after the needle-like recessed portions 15 of the mold 13 are filled with the drug-containing solution 22. The drug-containing solution 22 can be applied in the same manner as in the first embodiment. Next, as shown in FIG. 30, the drug-containing solution 22 is dried. For the drying, drying is stopped in a state in which moisture remains in the drug-containing solution 22 and the next base liquid feeding step is carried out. The drying is preferably stopped in a state in which the moisture content in the drug-containing solution 22 is 20% by weight or more.

Base Liquid Feeding Step

Figure 31:
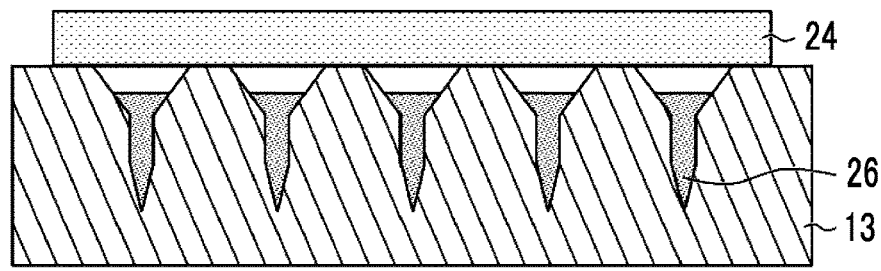
FIG. 31 is a diagram illustrating the other step of forming the polymer sheet.

Next, as shown in FIG. 31, the base liquid 24 is fed to the mold 13. For the feeding method, feeding can be carried out in the same manner as in the first embodiment. In addition, as the base liquid, a base liquid which is sterilized by sterile filtration as in the first embodiment is used.

Drying Step

Figure 32:
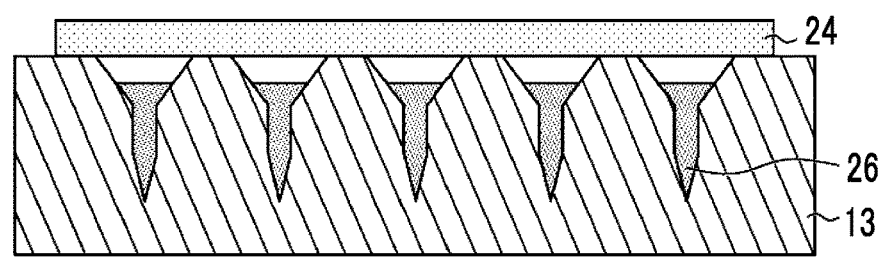
FIG. 32 is a diagram illustrating the other step of forming the polymer sheet.

Next, as shown in FIG. 32, the drug-containing solution 22 and the base liquid 24 are dried. The drying method is not particularly limited and the same method as in the first embodiment can be used to carry out drying. In the embodiment, in the drug solution drying step before the base liquid feeding step, drying is stopped in a state in which the moisture content of the drug-containing solution 22 is 20% by weight or more before the solution is completely dried and solidified, and the base liquid feeding step and drying step are carried out. Accordingly, the total drying time can be reduced compared to a case in which the drug solution is completely dried and solidified. The moisture content of the drug-containing solution 22 can be obtained from a change in weight by measuring the change in weight before and after drying.

In addition, the base liquid 24 is fed after the drug-containing solution 22 is half-dried and then the needle-like recessed portion 15 is covered by the base liquid 24. Accordingly, the drug-containing solution 22 in the needle-like recessed portion 15 can be dried under a high humidity condition. Since a difference in moisture concentration between the surface and the inside of the drug-containing solution 22 can be reduced by drying under a high humidity condition, the moisture concentration of the surface of the drug-containing solution 22 can be maintained at a certain level even in a case in which drying is carried out, and the tip end of the needle-like recessed portion can be effectively filled with the drug-containing solution 22.

Base Liquid Moving Step

Figure 33:
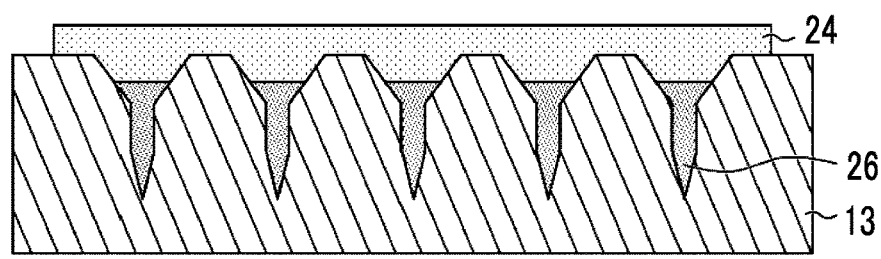
FIG. 33 is a diagram illustrating the other step of forming the polymer sheet.

The drug-containing solution 22 and the base liquid 24 are dried by the drying step and the base liquid 24 is moved into the needle-like recessed portion 15 after the average concentration of the solid contents of the base liquid is increased by 5% by weight or more from the average concentration of solid contents in the case of the base liquid feeding step (FIG. 33). In the embodiment, in the drying step, the drug-containing solution 22 is also dried in addition to the base liquid 24. However, since the drug-containing solution 22 has a much lighter liquid weight than the base liquid 24, the average concentration of the solid contents of the base liquid 24 can be obtained on the assumption that a change in weight before and after drying is set as a change in weight of the base liquid 24 before and after drying.

The base liquid moving step can be carried out by pressurizing the base liquid 24 from the surface side of the mold 13 on which the needle-like recessed portions 15 are formed by carrying out reduced pressure suction from the back surface side of the mold 13 as in the first embodiment.

Figure 34:
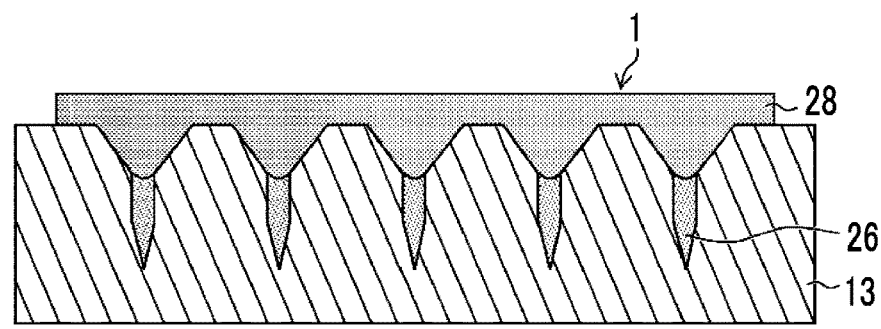
FIG. 34 is a diagram illustrating the other step of forming the polymer sheet.

The polymer sheet 1 including the drug-containing layer 26 and the non-drug-containing layer 28 is formed by further carrying out drying after the base liquid moving step (FIG. 34). After the polymer sheet 1 is formed, a peeling-off step is carried out in the same method as in the first embodiment to peel off the polymer sheet 1 from the mold 13. Thus, the transdermal absorption sheet 2 for medical use is produced.

EXAMPLES

Hereinafter, the present invention is further specifically described using examples of the present invention. Materials, usages, rates, the contents of treatments, the treatment procedures, and the like illustrated in the following examples may be appropriately changed unless the change departs from the spirits of the present invention. Thus, the scope of the present invention should not be interpreted in a limited manner based on the specific examples illustrated below.

EXAMPLES

Preparation of Mold

Figure 35:
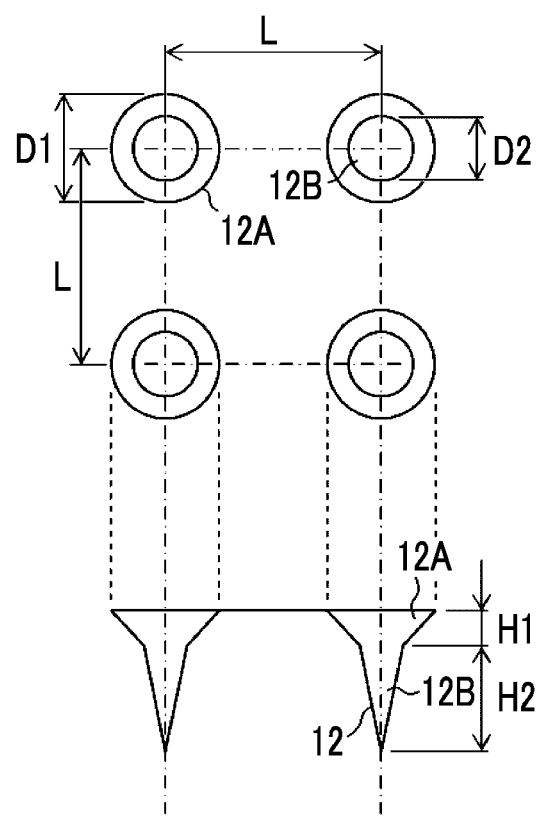
FIG. 35 is a plan view and a side view of an original plate.

As shown in FIG. 35, an original plate 11 was produced by grinding the surface of a smooth ALUMIGO plate having one side of 40 mm so as to form shape portions 12 with a needle-like structure that are arranged at a pitch L of 1,000 μm in a two-dimensional array with 10 rows and 10 columns. Each shape portion 12 with a needle-like structure includes a truncated cone 12A having a bottom surface diameter D1 of 500 μm and a height H1 of 150 μm and a cone 12B formed on the truncated cone 12A and having a diameter D2 of 300 μm and a height H2 of 500 μm.

A film having a thickness of 0.700 nm was formed on the original plate 11 using silicone rubber (SILASTIC-MDX4-4210, manufactured by Dow Corning Toray Co., Ltd.), thermally cured, and peeled-off. Thus, an inverted article of the silicone rubber was prepared. The inverted article of the silicone rubber was trimmed so as to leave a planar portion with one side of 30 mm on whose central portion needle-like recessed portions were formed to be two-dimensionally arranged in 10 rows and 10 columns, and the obtained portion was used as a mold. The surface of the needle-like recessed portion where the opening portion is exposed was set as the surface of the mold.

Preparation of Drug-Containing Solution

Hydroxyethyl starch (manufactured by Fresenius Kabi) was dissolved into water to prepare a 4 wt % (weight percentage) aqueous solution. 1 wt % of human serum albumin (manufactured by Wako Pure Chemical Industries, Ltd.) was added to the solution as a drug to obtain a drug-containing solution. After the solution was prepared, the solution was exposed to the environment of a reduced pressure of 3 kPa for 4 minutes and deaeration was carried out.

Preparation of Polymer Solution Becoming Base Material

Dextran 70 (manufactured by Meito Sangyo Co., Ltd.) was dissolved in water to prepare a 40 wt % (weight percentage) aqueous solution. After the solution was prepared, the solution was exposed to the environment of a reduced pressure of 3 kPa for 4 minutes and deaeration was carried out.

Drug Solution Filling Step and Drug Solution Drying Step

A drug solution filling apparatus includes a driving portion that has an X-axis driving portion and a Z-axis driving portion controlling relative position coordinates of the mold and the nozzle, a liquid feeding apparatus (super small amount fixed-quantity dispenser SMP-III manufactured by Musashi Engineering, Inc.) on which the nozzle can be mounted, a suction base to which the mold is fixed, a laser displacement gauge (HL-C201A manufactured by Panasonic Corporation) that measures a surface shape of the mold, a load cell (LCX-A-500N manufactured by Kyowa Electronic Instruments Co., Ltd.) that measures a nozzle pressing pressure, and a control system that controls the Z axis based on data of measurement values of the surface shape and the pressing pressure.

The mold was installed on the horizontal suction base such that the surface thereof was positioned on the upper side. The mold was fixed to the suction base by pressure reduction with a suction pressure of 90 kPa gauge pressure the back surface direction of the mold.

A stainless steel nozzle having the shape shown in FIG. 15 was prepared, and a slit-shaped opening portion having a length of 12 mm and a width of 0.2 mm was formed at the center of a lip portion having a length of 20 mm and a width of 3 mm. This nozzle was connected to a drug solution tank. The drug solution tank and the nozzle were filled with 3 mL of a drug-containing solution. The nozzle was adjusted such that the opening portion was parallel to the first row of a plurality of needle-like recessed portions formed in the surface of the mold. The nozzle was pressed against the mold with a pressure (pressing force) of 0.144 kgf/cm$^2$ (1.4 N/cm$^2$) at a position spaced apart from the first row with an interval of 2 mm therebetween in a direction opposite to a second row. While being pressed, the nozzle was moved at 1 mm/sec in a direction perpendicular to a length direction of the opening portion while the Z axis was controlled such that the pressing force changed within ±0.05 kgf/cm$^2$ (0.49 N/cm$^2$). Simultaneously, by the liquid feeding apparatus, the drug-containing solution was discharged from the opening portion for 10 seconds at 0.31 μL/sec. The movement of the nozzle was stopped at a position spaced apart from a tenth row of the plurality of needle-like recessed portions arranged two-dimensionally with an interval of 2 mm therebetween in a direction opposite to a ninth row, and the nozzle was separated from the mold.

The drug solution filling the needle-like recessed portions of the mold was dried and the drug was unevenly distributed at a tip end.

Base Liquid Feeding Step and Drying Step

The mold in which the drug solution had been dried was fixed to the suction apparatus. A silicone rubber form having a diameter of 16 mm and a thickness of 0.5 mm was installed such that the needle-like recessed portions of the mold were positioned at the center. About 100 mg of the polymer solution which became the base material of the transdermal absorption sheet for medical use was applied to the inside of the opening portion of the form.

After the solution was applied, the solution was dried under the conditions of a temperature of 23° C., a humidity of 60% RH, and a wind speed of 0.1 m/sec.

A change in weight before and after drying was measured and the average concentration of the solid contents of the base liquid was obtained from the change in weight. At the time when the average concentration of solid contents reached the concentration shown in Table 1 by drying, suction was carried out from the back surface side of the mold and the base liquid was moved into each of the needle-like recessed portions.

After the base liquid was moved into each of the needle-like recessed portions, the base liquid was dried and solidified by continuously carrying out drying.

Peeling-Off Step

The polymer layer was peeled off from the mold so as to be turned over from the end portion and thus a transdermal absorption sheet for medical use having needle-like protruding portions having a two-dimensionally arrangement structure in which the human serum albumin was unevenly distributed at the tip end was produced.

The drying time was compared using Comparative Example 1, as a reference, in which the base liquid moving step was carried out immediately after the base liquid feeding step, and evaluation was conducted based on the following standards. The results are shown in Table 1.

A . . . Significantly improved as compared with the reference

B . . . Improved as compared with the reference

C . . . Equal to the reference as compared with the reference

D . . . Immeasurable

TABLE 1

|  | Concentration immediately after base liquid feeding step | Concentration before base liquid moving step | Evaluation (Drying time) |
| --- | --- | --- | --- |
| Example 1 | 40 wt % | 75 wt % | A |
| Example 2 | 40 wt % | 55 wt % | A |
| Example 3 | 40 wt % | 45 wt % | B |
| Comparative Example 1 | 40 wt % | 40 wt % | Reference |
| Comparative Example 2 | 40 wt % | 80 wt % | D |
| Comparative Example 3 | 40 wt % | 41 wt % | C |

In Examples 1 to 3 in which the average concentration of the solid contents of the base liquid was increased by 5 wt % or more by drying before the base liquid moving step after the base liquid feeding step, the drying time was improved compared to Comparative Example 1 as the reference. Further, in Examples 1 and 2 in which the average concentration of the solid contents of the base liquid was increased by 15 wt % or more, the drying time was significantly improved compared to Comparative Example 1.

In addition, in Comparative Example 2 in which the average concentration of the solid contents of the base liquid before the base liquid moving step was 80 wt %, the base liquid was not allowed to flow, the base liquid was not moved to the needle-like recessed portions in the base liquid moving step, and needles could not be formed. A difference between the drying time in Comparative Example 3 in which the average concentration of solid contents before the base liquid moving step was 41 wt % and the drying time in Comparative Example 1 was not observed.

EXPLANATION OF REFERENCES

1: polymer sheet
2: transdermal absorption sheet for medical use
4: needle-like protruding portion
5: truncated cone portion
6: needle portion
10: microneedle
10A: ridge line
10B: microneedle tip end
10C: quadrangular pyramidal surface
11: original plate
12: shape portion
12A: truncated cone
12B: cone
13: mold
14: frame
15: needle-like recessed portion 15A: inlet portion
15B: intermediate recessed portion
15C: tip end recessed portion
15D: air vent hole
18: mold complex
19: gas permeable sheet
20: base
22: drug-containing solution
24: base liquid
26: drug-containing layer
28: non-drug-containing layer (base material)
29: support
30: tank
32: pipe
34: nozzle
34A: lip portion
34B: opening portion
36: liquid feeding apparatus
40: substrate

What is claimed is:

1. A method of producing a transdermal absorption sheet for medical use comprising, in this order:
   a filtration step of carrying out sterile filtration on a base liquid not containing a drug;
   a base liquid feeding step of feeding the base liquid to a surface of a mold having needle-like recessed portions, tip ends of which are filled with a drug solution, the needle-like recessed portions being formed on the surface, while leaving a space between the drug solution and the base liquid;
   a drying step of drying the drug solution and the base liquid, wherein an average concentration of solid contents of the base liquid is increased by 30% by weight or more from an average concentration of solid contents of the base liquid in the base liquid feeding step;
   a base liquid moving step of moving the base liquid into each of the needle-like recessed portions of the mold in a state in which the average concentration of the solid contents is 75% by weight or less due to the drying step; and
   a peeling-off step of peeling off a transdermal absorption sheet for medical use formed by drying the drug solution and the base liquid.

2. The method of producing a transdermal absorption sheet for medical use according to claim 1,
   wherein the base liquid is moved into the needle-like recessed portions by carrying out suction from a side of the mold opposite to the surface on which the needle-like recessed portions are formed or by carrying out pressurization from the surface side of the mold on which the needle-like recessed portions are formed.

3. The method of producing a transdermal absorption sheet for medical use according to claim 1,
   wherein the base liquid feeding step is carried out in a state in which a moisture content of the drug solution is 20% by weight or more.

* * * * *